US006639213B2

United States Patent
Gillig et al.

(10) Patent No.: US 6,639,213 B2
(45) Date of Patent: Oct. 28, 2003

(54) PERIODIC FIELD FOCUSING ION MOBILITY SPECTROMETER

(75) Inventors: Kent J. Gillig, College Station, TX (US); David H. Russell, College Station, TX (US)

(73) Assignees: The Texas A & M University System, College Station, TX (US); Ionwerks, Houston, TX (US)

( * ) Notice: Subject to any disclaimer, the term of this patent is extended or adjusted under 35 U.S.C. 154(b) by 415 days.

(21) Appl. No.: 09/798,032

(22) Filed: Feb. 28, 2001

(65) Prior Publication Data

US 2001/0032930 A1 Oct. 25, 2001

Related U.S. Application Data

(60) Provisional application No. 60/193,659, filed on Mar. 31, 2000, and provisional application No. 60/185,781, filed on Feb. 29, 2000.

(51) Int. Cl.[7] .......................... H01J 49/00; B01D 59/44
(52) U.S. Cl. ...................... 250/286; 250/281; 250/282; 250/288; 250/287
(58) Field of Search ............................. 280/286, 281, 280/282, 288, 287

(56) References Cited

U.S. PATENT DOCUMENTS

| | | | |
|---|---|---|---|
| 4,855,595 A | 8/1989 | Blanchard | |
| 5,189,301 A | 2/1993 | Thekkadath | |
| 5,200,614 A | * 4/1993 | Jenkins | .................. 250/286 |
| 5,235,182 A | 8/1993 | Avida | |
| 5,280,175 A | 1/1994 | Karl | |
| 5,789,745 A | 8/1998 | Martin et al. | |
| 5,905,258 A | 5/1999 | Clemmer et al. | |
| 6,512,224 B1 | * 1/2003 | Miller et al. | .................. 250/286 |

OTHER PUBLICATIONS

Phys. Rev., vol. 164, 62 (1067).
J. Am. Soc. Mass Spectrom., 7, 101–106 (1996).

* cited by examiner

Primary Examiner—Nikita Wells
(74) Attorney, Agent, or Firm—Fulbright & Jaworski L.L.P.

(57) ABSTRACT

This invention is generally in the field of improved ion mobility spectrometry. The improvement lies in the use of periodic focusing electric fields that minimize the spatial spread of the migrating ions by keeping them in a tight radius about the axis of travel. The resulting enhancement in sensitivity is accomplished without a concomitant loss in resolution as would normally be expected when non-linear fields are used.

27 Claims, 11 Drawing Sheets

Fig. 5  Maximum on-axis deviation from a linear field

PERIODIC FIELD FOCUSING ION MOBILITY SPECTROMETER

This application claims priority to U.S. Provisional Application No. 60/193,659, filed Mar. 31, 2000, and to U.S. Provisional Application No. 60/185,781, filed Feb. 29, 2000.

The technology was developed with government support (NSF Reference No. CHE 9629966 and DOE Reference No. DE-FG03-ER14505). The government may have certain rights in the invention.

BACKGROUND OF THE INVENTION

Ion Mobility Spectrometry ("IMS") is a technique that separates ions in terms of their mobility with reference to a drift/buffer gas. The analysis is based on measuring the velocity which gaseous ions obtain while drifting a defined length through the buffer gas. Prior art mobility techniques are known as "time-of-flight" separation techniques if detection is based on time, or as "differential" separation techniques if ion detection is based on position. In either case the ion mobility can be determined from the ion drift velocity, $v_d$, and is inversely proportional to the electric field strength, E:

$$V_d = K_0 E$$

where $K_0$ is reported at 760 Torr and 273 K and is a function of the ion volume/charge ratio and can be related to ion size and shape through the measured collision cross-section.

In many instances the ion mobility chamber is designed to produce a linear constant electric field either constructed as a series of equally spaced electrodes connected through a resistor chain, or as a tube, which has been coated with a resistive material. In one case, U.S. Pat. No. 5,789,745 to Martin et al., a traveling potential well was used to transport ions of differing mobility in hopes of miniaturizing the drift cell while maintaining resolution, but no evidence of addressing resolution is shown. U.S. Pat. No. 5,189,301 to Thekkadath constructed a cup shaped electrode, creating a non-linear field to focus ions to a detector thereby increasing sensitivity by decreasing losses due to diffusion. U.S. Pat. No. 4,855,595 to Blanchard has also used nonlinear fields for the purpose of controlling ions by trapping ions in a potential well to normalize drift differences and increase selectivity. The '595 patent achieves ion trapping by using a sequence of electric fields; two of which move ions in the direction of the collector while the other field reverses the migration for a time by moving the ions away from the collector.

U.S. Pat. No. 5,235,182 to Avida took a different approach, using slightly focusing electric fields formed by a particular electrode width to gap ratio to increase sensitivity and claiming increased resolution, but providing no substantial evidence therein. In fact, the resolution as reported by Avida was only one-third of prior art devices. The Avida drift tube owes its slightly focusing characteristics to the fringing fields seen in the areas near the electrodes and endplates. The use of only slightly focusing fields imposes fundamental limitations on the Avida instrument. Optimal realization of the advantages of the Avida instrument and method are limited to relatively high-pressure applications and those using a broad ionization source as opposed to those using pulsed ionization methods. In these cases, an only "slightly" focusing field will be insufficient to avoid a diminution in sensitivity because the traversing ions will be concentrated in the center of the drift tube where the focusing effects are non-existent. A major advancement of the present invention is the discovery that much more strongly focusing fields are obtainable using electrode configurations having dimensions outside the range of those taught by Avida. In this way, the novel dimensions and configurations taught herein are much better suited for IMS applications, which utilize pulsed ionization methods.

In one instance, Gillig constructed an IMS device using a homogeneous magnetic field to increase sensitivity by reducing ion losses due to diffusion in a linear electric field, taking advantage of the fact that a homogeneous magnetic field has no effect on mobility along the drift cell axis. It is well known in the art of spectrometry that the resolution performance of an ion mobility spectrometer is to a large degree controlled by the linearity of the electric field in the drift cell. To maximize resolution at a given voltage drop and pressure the electric field is kept as linear as possible and in fact any non-linearity will decrease resolution by increasing drift times along the axis of the instrument. Therefore, for a given voltage drop, the theoretically optimum result for an increase in sensitivity when using non-linear fields is the preservation of the analogous resolution obtained using linear fields.

Coupling of an ion mobility chamber to an orthogonal time-of-flight mass spectrometer was described in the literature in both the journal article by McKnight, L. G., et al., *Phys. Rev.*, 164, 62 (1967), and *The Mobility and Diffusion of Ions in Gases*, 68–72 (1973). Clemmer, et al., in U.S. Pat. No. 5,905,258, using a similar approach, teach improvements in IMS/MS which incorporate ionization techniques more suitable for biological applications. In one aspect of the present invention, a periodic focusing ion mobility spectrometer is coupled to an orthogonal time-of-flight mass spectrometer for mass analysis purposes resulting in an improved IMS/MS.

The challenges in the field of spectrometry have continued to increase with demands for more and better techniques having greater flexibility and adaptability. Therefore, there exists a need for a new system and method for separating and analyzing ions.

SUMMARY OF THE INVENTION

In a specific embodiment of the present invention there is an apparatus for separating and analyzing ions, comprising an ion source to generate ions an ion mobility chamber positioned to receive the ions from the ion source and capable of producing a periodic focusing electric field. The ion mobility chamber comprises a plurality of outer ring electrodes and a plurality of outer ring inter-electrode gaps coupled to the outer ring electrodes, a plurality of inner ring electrodes coaxial with the outer ring electrodes and equally spaced to form an inner drift tube. The ratio of the drift tube diameter to the electrode width of any individual inner ring electrode is less than four. A resistor chain is coupled to the outside of the ion mobility chamber to apply a potential to both the outer and inner ring electrodes and an endplate is coupled to the ion mobility chamber, the endplate having an ion aperture to expel the ions. Additionally, a plurality of lenses is coupled to the ion aperture and a plurality of electrostatic steering plates coupled to the lenses and a detector coupled to the lenses.

In another specific embodiment, an apparatus for separating and analyzing ions comprises an ion source to generate ions, an ion mobility chamber positioned to receive the ions from the ion source and capable of producing a periodic focusing electric field. The ion mobility chamber comprises a plurality of ring electrodes equally spaced to form a drift tube and a plurality of inter-electrode gaps adjacent to the ring electrodes wherein the ratio of the drift tube diameter to the electrode width of any individual ring electrode is less than four. A resistor chain is coupled to the outside of the ion mobility chamber to apply a potential to the ring electrodes and an endplate is coupled to the ion mobility chamber, the endplate having an ion aperture to expel ions. A plurality of lenses is coupled to the ion aperture, a plurality of electrostatic steering plates coupled to the lenses and a detector is also coupled to the lenses.

Another embodiment involves a method of separating and analyzing ions in the presence of a gas comprising the steps of generating ions from an ion source and separating ions in terms of their mobility. The separating step comprises transporting the ions in a periodic focusing electric field. The ions are thereafter detected.

A further embodiment involves a method for transporting ions in the presence of a gas by transporting ions in a periodic focusing electric field thereby increasing the transmission efficiency of the ions from a high pressure source to high vacuum.

In the preferred apparatus embodiment using multiple coaxial series of electrodes, the ratio of the distance from the inner surface of the outer ring of electrodes to the spectrometer axis to the distance from the inner surface of the inner ring of electrodes to the spectrometer axis is less than six.

Additionally, in the preferred embodiment for all apparatuses, the detector is a mass spectrometer, preferably a time-of-flight mass spectrometer and more preferably, the drift tube of the TOFMS is orthogonal to the drift tube of the ion mobility cell.

In an alternative embodiment, the apparatus allows the multiple series of electrodes to be offset from one another by a distance up to and including one electrode width. In some cases, the series of electrodes are replaced with resistively coated metal helixes. These helixes may also be offset up to and including one unit helix thickness, such thickness being equal to thickness of the wire making up the helix.

In the preferred embodiment, the ionization source is a matrix-assisted laser desorption source.

In another embodiment, the method for separating and detecting ions using a mass spectrometer for detection.

Additionally, in the preferred method embodiment, the detector is a mass spectrometer, preferably a time-of-flight mass spectrometer and more preferably, the drift tube of the TOFMS is orthogonal to the drift tube of the ion mobility cell.

In an alternative embodiment, the method employs one series of electrodes to be offset from another series by a distance up to and including one electrode width. In some cases, the series of electrodes are replaced with resistively coated metal helixes. These helixes may also be offset up to and including one unit helix thickness, such thickness being equal to thickness of the wire making up the helix.

In the preferred embodiment, the method uses matrix-assisted laser desorption ionization.

In an alternative embodiment, a method of transporting ions in the presence of gas is described outside the context of ion mobility spectrometry. The method utilizes periodic field focussing in the single electrode series and in the multiple electrode series embodiment. In either embodiment the electrodes may be substituted by metal helixes. In the multiple series embodiment, the electrodes and helixes may be offset as described above.

The present invention provides an IMS instrument having improved sensitivity over the prior art while simultaneously preserving the resolution. In so doing, the improved IMS is particularly amenable to applications where the pressure is from 1 to hundreds of Torr with an ionization source and a small sampling aperture for sampling ions after separation in the drift tube.

DETAILED DESCRIPTION OF THE INVENTION

As used herein, "drift tube diameter" is defined as the distance from the spectrometer axis to the electrode surface nearest to the spectrometer axis. In the case of multiple coaxial series of electrodes, this distance refers to that from the spectrometer axis to the electrode surface nearest to the spectrometer axis of the innermost coaxial series of electrodes. It is synonymous with the expression "inner diameter".

As used herein, "electrode width" is defined as the ratio of the length, L, of the drift region to the total number, N, of periods in the drift region minus the inter-electrode gap width, G; alternatively, it is mathematically defined as (L/N)−G.

As used herein, "focusing", when used in reference to a beam of ions, is defined as any imaging event that reduces the spread of the ion beam to any degree; it does not necessarily require that the reduction result in a focus point.

As used herein, "gaps of a metal helix" are the distances between the wire or wire-like structures which make up the metal helix.

As used herein, a "heterogeneous electric field", or alternatively, an "electric field exhibiting substantial heterogeneity" is an electric field in which the deviation from a linear electric field along the spectrometer axis at each electrode or electrode gap is greater than 0.10%.

As used herein, a "homogeneous electric field", or alternatively, an "electric field exhibiting substantial homogeneity" is an electric field in which the maximum deviation from a linear electric field along the spectrometer axis at each electrode or electrode gap is no more than 0.10%.

As used herein, the abbreviation "IMS" is defined as ion mobility spectrometry.

As used herein, "inter-electrode gap" is defined as any distance between electrodes that does not consist of an electrode; this may, for example, be an insulating material or air.

As used herein, "inter-electrode gap width" is defined as the distance between adjacent coaxial electrodes within a series.

As used herein, MALDI is defined as matrix assisted laser desorption ionization.

As used herein, the abbreviation "MS" is defined as mass spectrometry.

As used herein, "period" is defined as an electrode at a unique potential. N is the "number of periods for a given drift tube length" and is the number of electrodes having unique potentials.

As used herein, the expression "periodic focusing field" for a drift cell is defined as an electric field characterized by alternating periods of substantial homogeneity and substantial heterogeneity in which the regions of substantial heterogeneity as measured by % ($\Delta V/V$) is greater than about 0.1.

As used herein, "potential" means an electrical potential or synonymously, a voltage.

As used herein, "resistively coated metal helixes" are continuous metal wires or wire-like structures coated with any resistive material, generally taking the shape of a coil.

As used herein, the term "spectrometer axis" is defined as the major (lengthwise) axis of the spectrometer. This applies herein to both ion mobility instruments and mass spectrometric instruments.

As used herein, the abbreviation "TOFMS" is defined as time-of-flight mass spectrometry.

As used herein, a "unit helix thickness" is the width of the wire or wire-like structure of a resistively coated metal helix.

% ($\Delta V/V$) is defined as the percentage deviation from a linear electric field along the spectrometer axis at each electrode or electrode gap.

The present invention is an apparatus and method for separating and analyzing ions in a gaseous medium, thereby enabling high sensitivity of charged species while maintaining resolution comparable to that achieved in high resolution drift tubes known in the art. The apparatus comprises a plurality of coaxial electrodes with the ratio of the inter-electrode gap width to the electrode width being approximately less than one and the ratio of the drift tube diameter to the electrode width of any individual electrode is less than four. In the preferred embodiment, there is a plurality of coaxial electrodes comprising a second (inner) set of electrodes in addition to the first (outer) set of electrodes, wherein the inner diameter of the outer set of electrodes to the inner diameter of the enclosed electrodes being approximately less than six. The coaxial inner electrodes are equally spaced to form an inner drift tube, which produces a spatially periodic field when the outer electrodes are linearly displaced by a distance up to an including one electrode width. This displacement allows a perturbing electric field from the outer coaxial series of electrodes to penetrate the electric field of the inner coaxial series of electrodes. These penetrating fields result in the focusing regions of heterogeneity of the resultant field of the drift region The electric field perturbation effect of the electrode offset is maximized when the relative displacement is exactly one electrode width. For the coaxial inner electrodes, the ratio of the drift tube diameter to the electrode width of any individual inner ring electrode is less than four. Ions encountering the spatially periodic field so produced experience areas of focusing and defocusing in a sequential pattern.

Ions can be produced by any number of means including in part electrospray ionization, laser ionization, photoionization, electron ionization, thermal ionization, chemical ionization, electric field ionization, surface ionization, radioactive ionization, discharge ionization, multiphoton ionization, and matrix assisted laser desorption ionization ("MALDI"). Pulsed ionization techniques such as MALDI are preferred as the initial spatial spread of ions prior to mobility separation is kept to a minimum. Once formed ions are made to flow by a suitable arrangement of electric fields, they enter the inner electrodes and encounter a periodic combination of constant linear and nonlinear electric fields. Then the ionized chemical species are separated by mobility at a resolution comparable to that obtained with a linear field ion mobility chamber yet detected with a sensitivity far surpassing prior art instrumentation. Ions exit the ion mobility chamber through an aperture and are either focused into the source region of a time-of-flight mass spectrometer positioned perpendicular to the drift cell axis to enable mass analysis of the mobility separated ions, or focused onto a detector located on axis with the ion mobility chamber to enable mobility analysis of the emerging ions.

Figure 1:
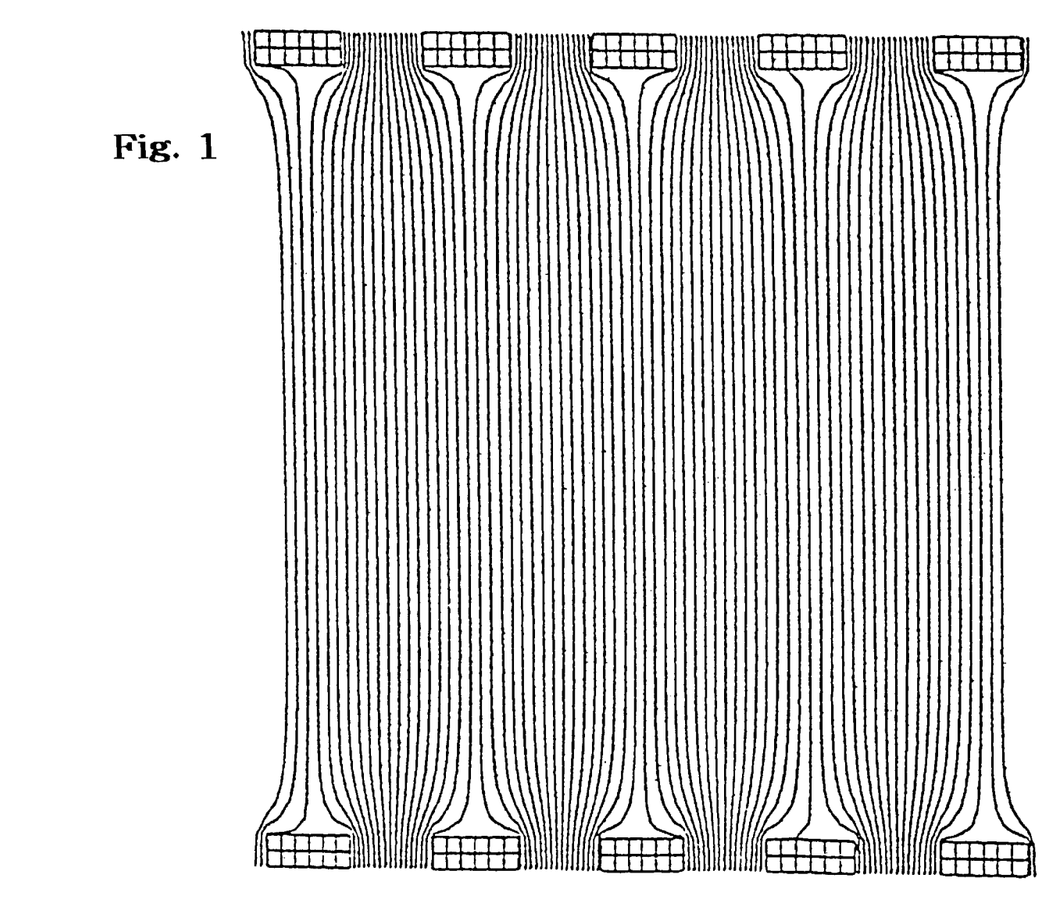
FIG. 1 is a plot of equipotential lines within a prior art ion mobility chamber to approximate a linear electric field.

Periodic focusing is accomplished by introducing substantial heterogeneity in the electric field that exists at the spectrometer axis. FIG. 1 shows the equipotential lines of a prior art device displaying a linear electric field. In such a device, under low field conditions, ion diffusion perpendicular to the ion mobility chamber axis and ion diffusion parallel to the ion mobility chamber axis are equal. Therefore, diffusion loss is simply a function of drift time (Fick's law) and for reasons given above a high resolution linear field device will display low sensitivity. IN the equipotential lines of FIG. 1, there are areas of electric field non-linearity near the electrode surfaces, but typically the magnitude of these areas relative to the areas of field linearity is less than 1%. Additionally, the value of % ($\Delta V/V$) at the spectrometer axis is zero or very near zero (i.e., the field is substantially homogeneous at this point). This condition is insufficient to produce substantial increases in sensitivity. In order to achieve the advantages of the present invention, relative area of electric field non-linearity to electric field linearity is preferably greater than 10% and more preferably greater than 50%. The values of % ($\Delta V/V$) at the spectrometer axis should be at least 0.10. In this way, substantial areas of heterogeneity are experienced by ions at or near the drift tube axis as well as those closer to the electrodes. In non-periodic instruments, ions traversing the drift tube at or near the drift tube axis do not experience areas of substantial electric field heterogeneity.

Figure 2:
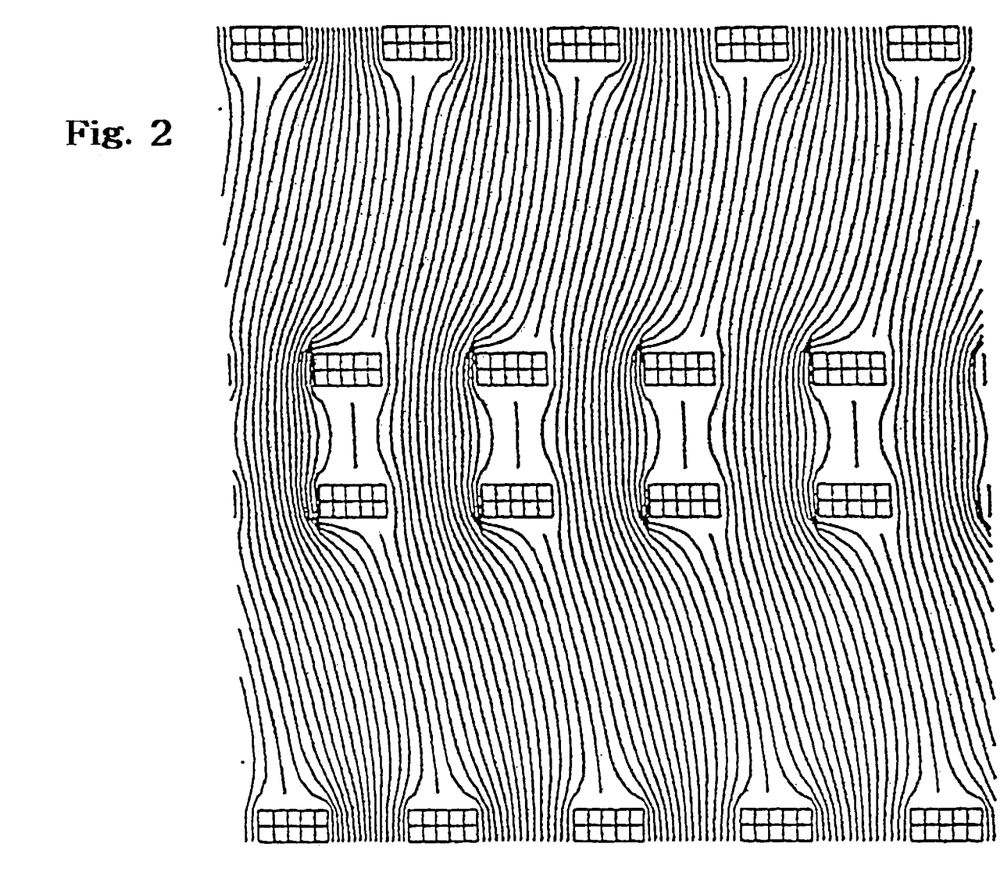
FIG. 2 is a plot of equipotential lines in an ion mobility chamber useful in the practice of the present invention illustrating its periodic nature.

FIG. 2 shows the equipotential lines in a section of one embodiment of the present invention displaying a series of periodic focusing fields. In this embodiment, two series of coaxial electrodes are used. The relative area of electric field non-linearity to that of electric field linearity is preferably greater than 10% and more preferably greater than 50%. The values of % (ΔV/V) at the spectrometer axis are at least 0.10. Additionally, the lengths of the alternating field regions of substantial heterogeneity and substantial homogeneity are not equal. The result is a periodic field that extends from the perimeter to the spectrometer axis. Ions traversing the drift tube experience the alternating periods of focusing and defocusing in every region of the tube. Periodicity is most easily achieved through the use of identical electrode and gap geometries, but is not limited to this mechanism. Use of differing geometries among the individual electrodes and gaps may also be used to realize the desired periodic fields.

Figure 3:
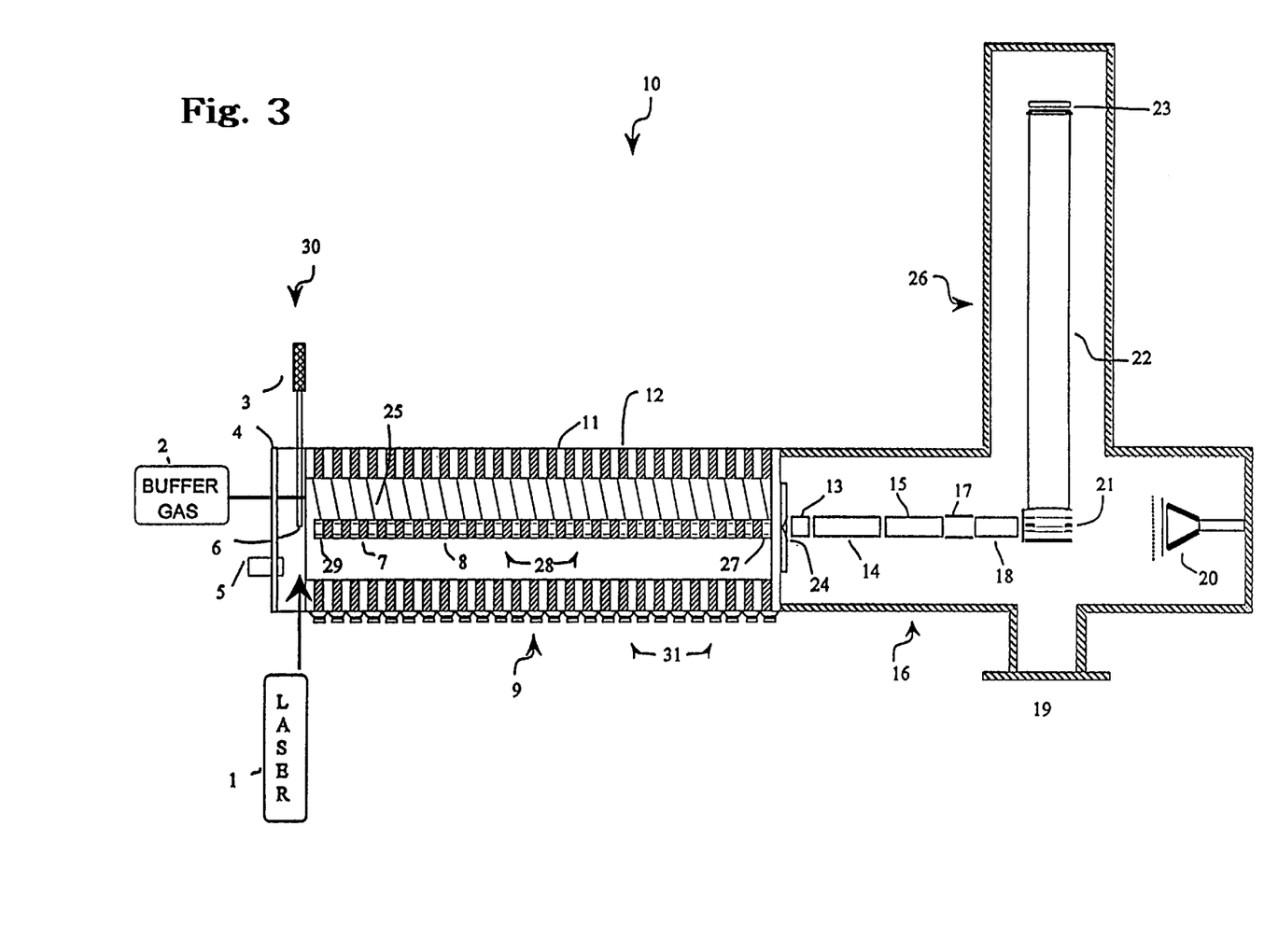
FIG. 3 shows a schematic of a spectrometer useful in the practice of the present invention.

FIG. 3 is a schematic view of one embodiment of a spectrometer 10 useful in the practice of the present invention. Spectrometer 10 comprises an ion mobility chamber 9, coupled at one end to an ion source 30, and at the other end to a lens system 16, followed by a detector 20, and a time-of-flight mass spectrometer 26 arranged perpendicular to the axis of ion mobility chamber 9. A laser 1 generates protonated molecular ions from a solid matrix/analyte sample introduced into ion mobility chamber 9 through vacuum interlock 3 and deposited on probe tip 6. The small packet of MALDI formed ions are directed to a set of inner electrodes 8 by a suitable electric field applied between endplate 4 and first inner electrode 29.

A periodic constant nonlinear/linear electric field is established within ion mobility chamber 9 by applying a linear potential drop across resistor chain 31 positioned outside ion mobility chamber 9. O-ring seals included in each outer electrode insulator 12 keep the outer electrode assembly vacuum tight. An identical potential drop is applied to inner electrodes 8 shifted linearly by one electrode width through a series of fine wires 25 connected between outer electrodes 11 and inner electrodes 8 and positioned so as to not disturb the electric field established between the inner electrode gaps 7. Ions are confined to the region inside inner electrodes 8 of FIG. 3. Ion motion within inner electrodes 8 is similar to electron motion in a periodic electron lens under vacuum/space charge conditions, or ion motion in a stacked-ring electrostatic ion guide or alternate gradient linear accelerator under vacuum conditions. These devices are stable if the axial kinetic energy of the ion or electron is greater than the experienced change in electric field along its trajectory giving a constant time-averaged axial kinetic energy. This is accomplished by injecting the ions or electrons under vacuum conditions with a high enough axial kinetic energy. In the present invention, with buffer gas 2 present, this is accomplished by the potential drop applied keeping the equilibrium axial kinetic energy sufficiently high. Ions are confined within inner electrodes 8 because they experience a time-periodic potential in the inertial frame.

Once inside the inner electrode assembly 28, ions drift through a series of equally spaced focusing and defocusing fields with the total ion drift time being equal to the sum of the individual inter-electrode drift times and the individual drift times within each electrode. For a large mobility range at a given field strength and pressure the calculated ion transmission approaches one hundred percent, with a spatial distribution of less than two square millimeters being dependent on the focusing field present between the distal inner electrode 27 and ion aperture 24. To increase the mobility resolution the drift field length is increased along with a corresponding increase in voltage applied. In contrast to prior art instrumentation, sensitivity of the present invention is independent of the length of ion mobility chamber 9. Therefore, a further technical advantage of the present invention is a high resolution mobility chamber capable of operating at low pressures and avoiding the disadvantages associated with prior art mobility chambers including diffusion losses, sampling loss through very small orifices, and stringent pumping requirements. Following ion mobility separation, ions are sampled through a 200 um–1 mm diameter ion aperture 24, focusing lens system 16 composed of four lens elements 13, 14, 15, 18, and electrostatic steering plates 17. With a mobility chamber buffer gas pressure of one to hundreds of Torr, the analyzer chamber 32 is kept below $1\times10^{-5}$ Torr by a suitable small high vacuum pump 19. Ions can then be focused onto a microchannel plate (MCP) detector assembly 20 to record the ion mobility distribution or focused into the time-of-flight source 21 where arriving ion packets are focused perpendicularly into flight tube 22. Mass spectra are then recorded with the MCP detector 23 using normal ion counting techniques. The acquired mass spectra can either be used for m/z identification/verification or plotted as a function of ion mobility drift times.

Figure 4:
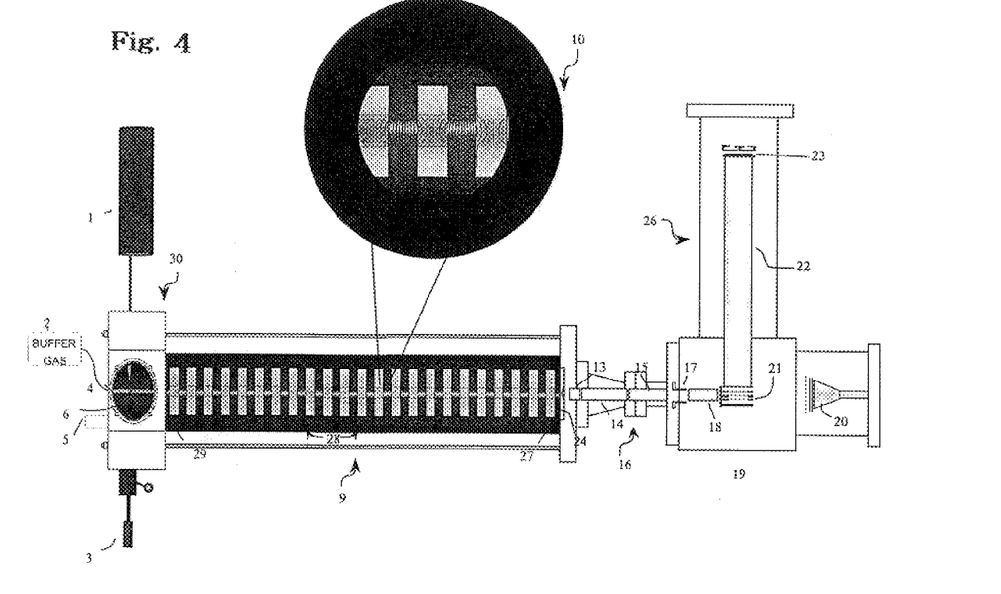
FIG. 4 shows a schematic of an alternative spectrometer useful in the practice of the present invention.
Figure 5:
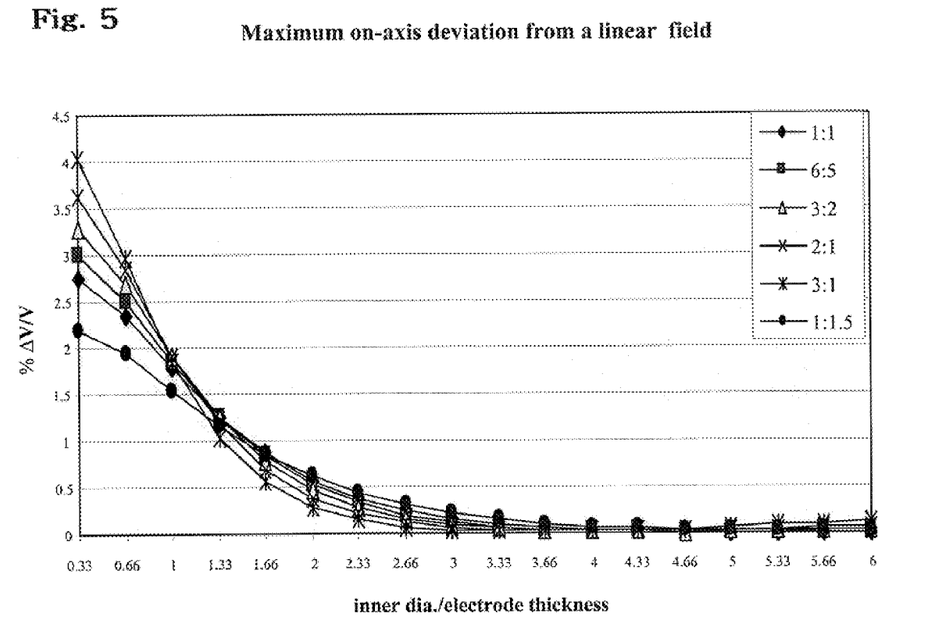
FIG. 5 is a plot, for an electrode system consisting of a single series of coaxial electrodes, of internal diameter/electrode width versus on-axis field heterogeneity ($\%\Delta V/V$). Data for a number of different (electrode width/inter-electrode gap width) values are shown.

The same or similar periodic focusing properties can be obtained using different electrode configurations. Another embodiment of a simplified spectrometer useful in the present invention is schematically shown in FIG. 4. Like numerals refer to like parts and correspond to those illustrated in FIG. 3. Notably, the embodiment depicted in FIG. 4 has only one coaxial series of electrodes. Note that in the absence of the outer series of coaxial electrodes, there are no penetrating fields perturbing the field within the inner ring of coaxial electrodes; thus the periodic field becomes symmetrical. FIG. 5 shows data on the ratio of electrode inner diameter (i.e., drift tube inner diameter) to electrode width plotted against the percentage of heterogeneity (%ΔV/V) of the field for a number of systems having a single series of coaxial electrodes. Note that the calculated deviation from a linear field is on-axis; i.e., along the centerline of the drift tube. The systems differ by the electrode width to inter-electrode gap width (FIG. 5). Notable from the figure is that substantial increases in field heterogeneity (and, as a result focusing strength) are not realized until the inner diameter to electrode width is less than about 4. Most notably, this is irrespective of the ratio of the electrode width to inter-electrode gap width within a coaxial series of electrodes. In light of the independence of focusing strength on the ratio of electrode width to inter-electrode gap width, it is clearly most advantageous to limit the ratio of inter-electrode gap width to electrode width to values less than 1:1. In such cases, a greater number of electrodes may be used for a given drift tube length. This manifests itself in a greater number of periods for a given drift tube length, thereby enhancing the beneficial effects of periodic focusing experienced by the ions traversing the drift tube. In this way, drift tubes of lengths useful for real world analyses may be used while continuing to realize the advantages of periodic focusing. The plot shown in FIG. 5 thus indicates that the best embodiment is realized using small inner diameters and where the ratio of the electrode width to inter-electrode gap width is greater than unity.

To further demonstrate the significance of inner diameter to total cross-sectional electrode width to the onset of periodicity, we can now view the problem from a different perspective. The effects of source size and detector size further illustrate the point. We now use the probability of an ion reaching the fringing fields of the drift cell and being turned back by the fields (spurious ions) as a measure of the drift cell homogeneity or periodicity with respect to source and end boundary conditions. Defining $r_0$ as the radius of the ion source, $r_1$ as the detector radius (aperture radius in one embodiment of the present invention), and $r_2$ as the drift region radius, then the minimum diffusion distance for ion to be turned back by the fringing fields is equal to:

$$(r_2-r_0)+(r_2-r_1)$$

and the probability, P, of an ion being turned back by the fringing fields is $$P=\exp[-(2r_2-r_1-r_0)^2/4D_Tt]$$

where $D_T$ is the transverse diffusion coefficient and t is time.

For high accuracy drift tube experiments with a sampling aperture a value for P of 0.001 is small enough that wall effects can be ignored. The probability corresponding to the example given in the maximum deviation plot assuming a value of less than 4 is equal to approximately 0.2 to 0.3. Depending on the source radius and detector radius an alternative definition of drift cell homogeneity could be used and an approximate value for the purpose of periodically focusing ions in a drift cell is 0.1 or a 10% probability that an ion will be turned back by fringing fields before reaching the detector.

Figure 6:
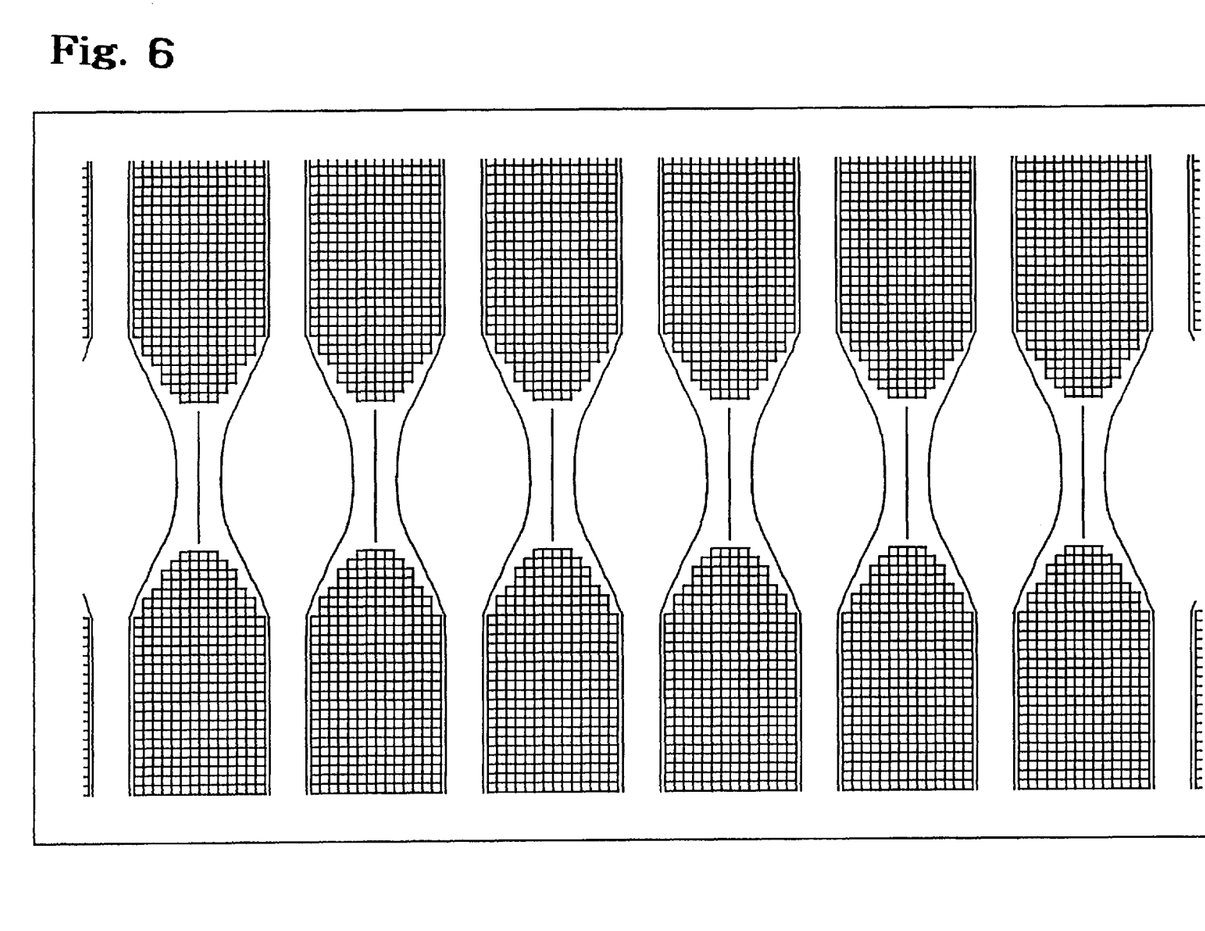
FIG. 6 demonstrates an embodiment in which the individual electrodes have been machined to possess hyperbolic characteristics.

One skilled in the art recognizes that other embodiments of the present invention are available that result in the same or similar periodic focusing properties. Examples of such forms include, but are not limited to, constructing the outer electrodes as a single unit coated with a resistive material, the inner or outer rings of inter-electrode gaps made of, or coated with, resistive material, a plurality of electrode lenses, etc., connected through a resistor chain across which a potential is applied, a single helix coated with resistive material wherein the pitch and dimensions of the helix are chosen so as to produce similar focusing properties, the outer electrodes replaced by a grounded cone, or the inner and outer electrodes replaced by two helices, coated with resistive material, and displaced from one another by a distance up to and including one helix width. The last mentioned example is analogous to that seen in the offsetting of two coaxial series of electrodes. One skilled in the art also recognizes that a periodically focused mobility separated beam of ions can be maintained within a length of multiple magnetic lenses. A further embodiment of the present invention defines the individual electrodes to optimized dimensions so that the electric field within the ion mobility spectrometer is improved. For example, the individual electrodes may be machined so that they possess hyperbolic characteristics as illustrated in FIG. 6, which shows such a structure along with the resulting equipotential lines. As with its ion optical counterpart, a hyperbolic lens structure possess fewer aberrations than cylindrical or aperture lenses so that the periodic focusing and defocusing fields are uniform and not as dependent on the off axis distance. The result is not only an increase in ion mobility resolution but also sensitivity since fewer ions are lost to the electrodes.

The resolution of prior art devices is determined by a combination of the effect of a finite pulse width of originating ions and the total potential drop experienced by the ions. These two effects are known as pulse width and diffusion limited resolution, respectively. In one embodiment of the present invention, MALDI is the preferred ionization method and the ion packet formed is of extremely short duration and composed of a limited number of ions. Therefore, the resolution of a MALDI ion mobility spectrometer is diffusion limited and predominantly a function of the applied potential. This is verified by observing a constant increase in resolution with voltage, i.e., the resolution does not reach a maximum value. The maximum potential that can be applied is determined by the discharge properties of buffer gas 2 employed (see FIGS. 3 and 4) which restrict high-resolution devices to be of sufficient length and operate at high pressures. When coupled to a mass spectrometer, diffusion loss in the mobility chamber and sampling efficiency through the required aperture(s) and interface, place limits on the attainable sensitivity even with the use of ion counting techniques.

Figure 7:
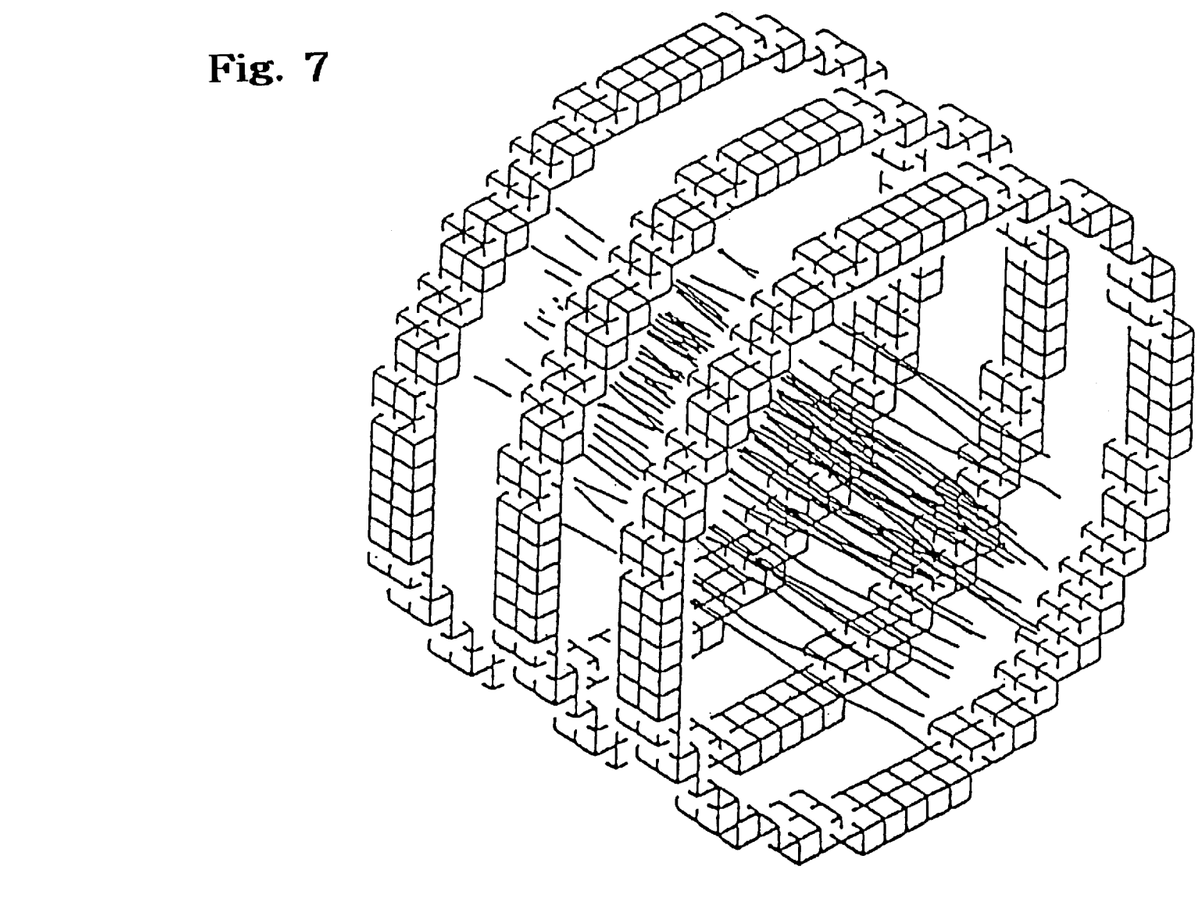
FIG. 7 is a trajectory calculation showing the spatial distribution of ions arriving at an endplate in a prior art instrument using a linear field.

FIG. 7 shows an ion trajectory calculation of m/z 720 ions arriving at an endplate in a linear field (prior art) device 1 meter long, with one Torr helium and 30 V/cm applied electric field. Note that even with the use of an electric field considered to be in the high field regime, ions are dispersed over a very large area and transmission through a sampling aperture would be as low as $1 \times 10^{-6}$; making detection very difficult if not impossible.

Figure 8:
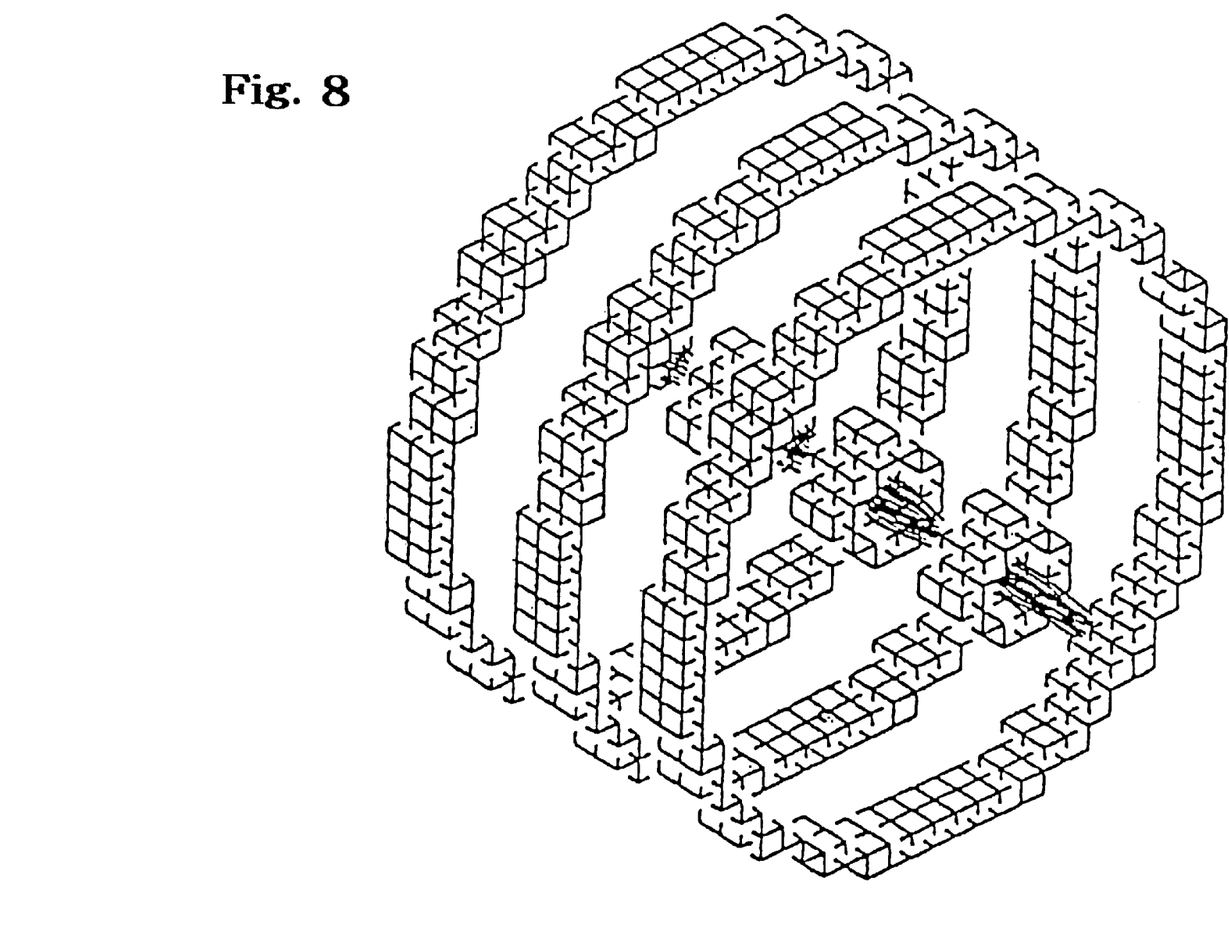
FIG. 8 is a trajectory calculation showing the spatial distribution of ions arriving at an endplate using the coaxial periodic focusing of the present invention.

FIG. 8 shows ion trajectory calculations of m/z 720 ions arriving at an endplate in a 1 meter long coaxial periodic focusing ion mobility spectrometer with 1 Torr helium and 30 V/cm applied electric field. The trajectories demonstrate that the transmission efficiency of the present invention is orders of magnitude greater than that exhibited by prior art devices. Ion motion is sinusoidal in nature. For an ion of m/z 720 with $K_0$ equal to 4.31, an ion mobility chamber consisting of one hundred focusing electrodes one meter in length with a static background pressure of one Torr helium and in a 30 volt/cm electric field will experience a time periodic potential in the inertial frame at an effective frequency of 31.2 kilohertz. This is sufficient to not only confine ions along the centerline of the ion mobility chamber but also to time average any fluctuations in ion drift time caused by nonlinear deviations in the electric field, i.e., the effect on mobility resolution is negligible. Therefore, a periodic focusing ion mobility spectrometer as described can be constructed to whatever length is necessary to provide sufficient resolution yet maintain high transmission efficiency with a corresponding increase in sensitivity.

Figure 9:
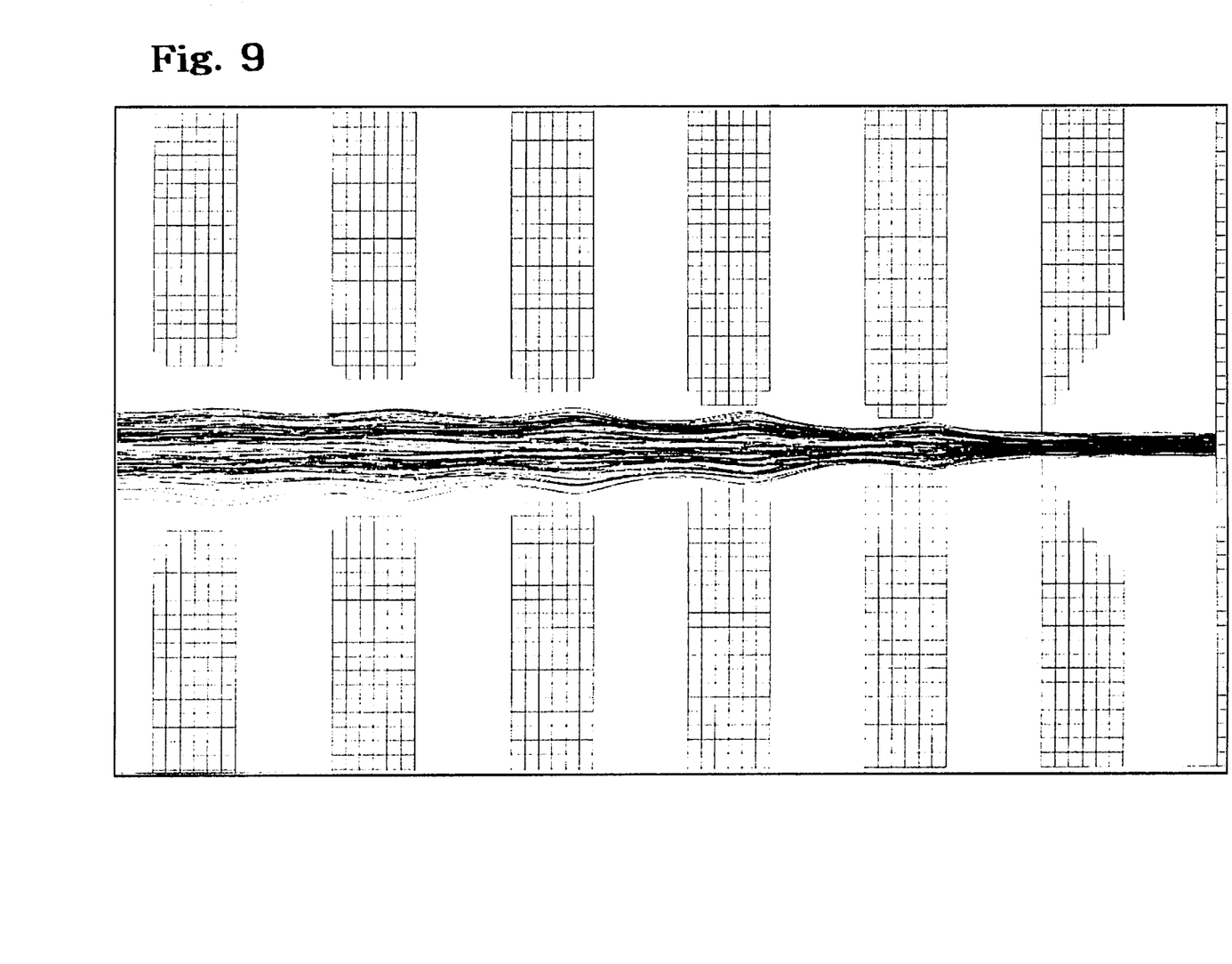
FIG. 9 demonstrates the ion trajectories obtainable using an embodiment of the present invention in which the last few electrodes have a decreasing inner radius.

FIG. 9 demonstrate the ion trajectories obtainable using an embodiment of the present invention in which the last few electrodes have a decreasing inner radius. The figure was constructed from calculated ion trajectories for m/z 720 ions experiencing elastic collisions with helium at a pressure of 1 Torr and at 298 K. The sequential periods of focusing and defocusing narrows the spatial distribution of ions as they traverse the drift cell. This particular embodiment improves the ion transmission an estimated order of magnitude over a device consisting of electrodes of the same inner radius, although the overall resolution may decrease somewhat. Such a device can be coupled to a periodic ion mobility spectrometer or any ion mobility spectrometer or high-pressure ion source as a differentially pumped interface to increase ion transmission from a region of high pressure to a detector. This embodiment is particularly advantageous wherein the mobility-separated ions are introduced into a mass spectrometer or other low-pressure region.

Figure 10:
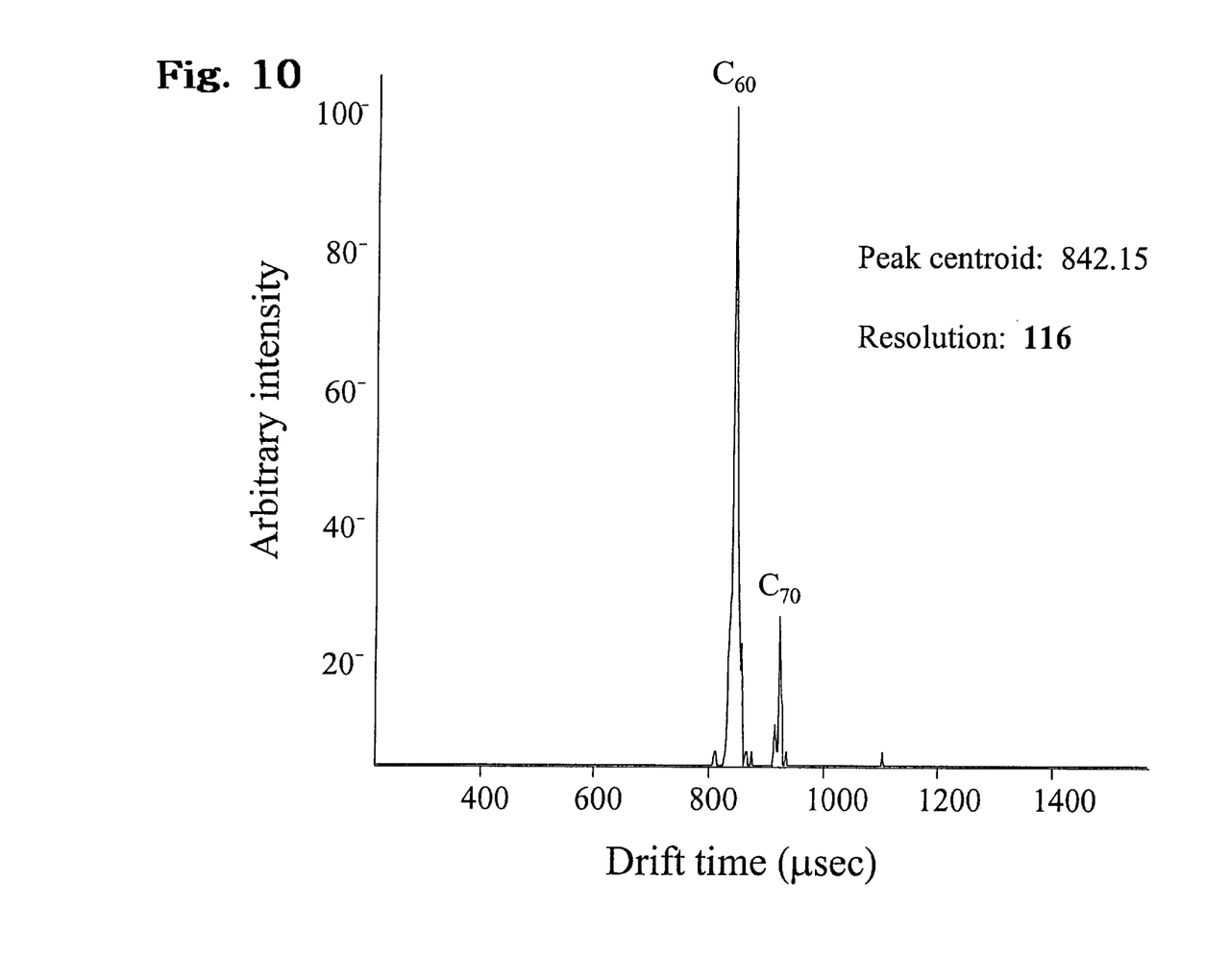
FIG. 10 is a high resolution ion mobility spectrum of laser desorbed $C_{60}$ and $C_{70}$ obtained using the present invention.

FIG. 10 shows an ion mobility arrival time distribution of laser desorbed $C_{60}$ and $C_{70}$ taken on axis detector located behind the periodic ion mobility drift cell. The periodic drift length was 30 cm, the pressure was approximately 4 Torr helium, and a potential of 1400 volts was applied. The resolution of the peak for $C_{60}$ determined by its full width at half height is 116. This resolution is significantly greater (approaching two-fold) than the calculated attainable resolution of 69 for a linear field ion mobility spectrometer operated with the same voltage. This result clearly demonstrates the performance characteristics of one embodiment of the present invention and in fact the resolution of the periodic spectrometer did not decrease due to ions experiencing periodic nonlinear electric fields, but rather, increased.

Figure 11:
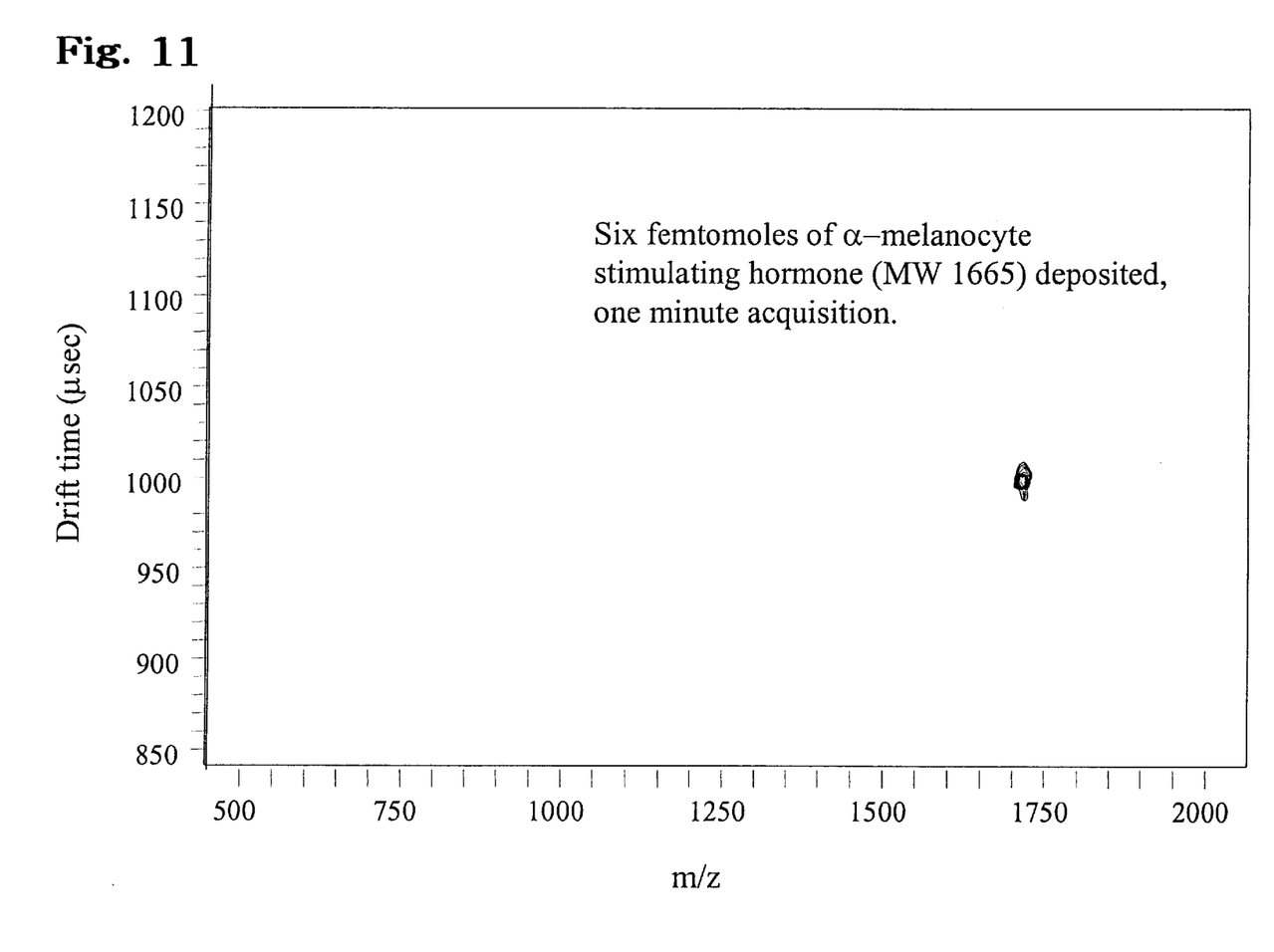
FIG. 11 is a contour plot of ion mobility drift time versus mass-to-charge ratio obtained using the present invention of six femtomoles of deposited peptide.

To demonstrate the sensitivity of the periodic spectrometer, a limit of detection experiment was performed. A single digit femtomole amount of peptide material was co-deposited with α-cyano-4-hydroxycinnamic acid as a matrix on a probe tip and ionized by MALDI in the spectrometer source. The 337 nm nitrogen laser was operated at 20 Hz and mass spectra of ions were accumulated for one minute over a large range of ion mobility arrival times. The resulting mobility-mass contour plot is shown in FIG. 11. This limit of detection is comparable to that obtained with a prior linear field ion mobility spectrometer with a 3 cm drift length.

Although embodiments of the invention and their advantages are described in detail, a person skilled in the art could make various alternations, additions, and omissions without departing from the spirit and scope of the present invention as defined by the appended claims.

REFERENCES CITED

All patents and publications mentioned in the specification are indicative of the level of those skilled in the art to which the invention pertains. All patents and publications are herein incorporated by reference to the same extent as if each individual publication was specifically and individually indicated to be incorporated by reference.

U.S. PATENT DOCUMENTS

U.S. Pat. No. 5,235,182 August 1993 Avida et al.
U.S. Pat. No. 5,189,301 February 1993 Thekkadath
U.S. Pat. No. 5,789,745 August 1998 Martin et al.
U.S. Pat. No. 4,855,595 August 1989 Blanchard, et al.
U.S. Pat. No. 5,905,258 May 1999 Clemmer et al.

OTHER PUBLICATIONS

Guan, S.; Marshall, A., *J. Am. Soc. Mass Spectrom.*, 7, 101–106 (1996).
Livingston, M. S.; Blewett, J. P., "Particle Accelerators", pp. 584–595, McGraw-Hill Book Co., Inc., 1962.
Gillig, K. J., "The Development of a Fourier Transform Ion Cyclotron Resonance Ion Mobility Spectrometer and Studies of Ion Motion in a Wiere Ion Guide Cell", Texas A&M University, Dissertation 1997.
Eiceman, G. A.; Karpas, Z., "Ion Mobility Spectrometry", CRC Press, Inc. 1994.
McKnight, L. G., et al., *Phys. Rev.*, 164, 62 (1967).
Mason, E. A.; McDaniel, E. W., "The Mobility and Diffusion of Ions in Gases", pp. 68–72, J. Wiley & Sons, 1973.
Gatland, I. R., "Case Studies in Atomic Physics IV", McDaniel, E. W., McDowell, M. R. C., Ed., North Holland Publishing Company: Amsterdam, 1975, p. 371.

One of skill in the art readily appreciates that the present invention is well adapted to carry out the objectives and obtain the ends and advantages mentioned as well as those inherent therein. Changes therein and other uses will occur to those skilled in the art which are encompassed within the spirit of the invention or defined by the scope of the pending claims.

What is claimed is:

1. An apparatus for separating and analyzing ions, comprising:
    an ion source to generate ions;
    an ion mobility chamber positioned to receive the ions from the ion source and capable of producing a periodic focusing electric field wherein the ion mobility chamber comprises:
    a plurality of outer ring electrodes;
    a plurality of outer ring inter-electrode gaps coupled to the outer ring electrodes;
    a plurality of inner ring electrodes coaxial with the outer ring electrodes and equally spaced to form an inner drift tube wherein the ratio of the drift tube diameter to the electrode width of any individual inner ring electrode is less than four; and,
    a resistor chain coupled to the outside of the ion mobility chamber to apply a potential to both the outer and inner ring electrodes;
    an endplate coupled to the ion mobility chamber, the endplate having an ion aperture to expel the ions;
    a plurality of lenses coupled to the ion aperture;
    a plurality of electrostatic steering plates coupled to the lenses; and,
    a detector coupled to the lenses.

2. The apparatus of claim 1 wherein the ratio of the distance from the inner surface of the outer ring of electrodes to the spectrometer axis to the distance from the inner surface of the inner ring of electrodes to the spectrometer axis is less than six.

3. The apparatus of claim 1 wherein the detector is a mass spectrometer coupled to the lenses.

4. The apparatus of claim 3 wherein the mass spectrometer is a time-of-flight mass spectrometer.

5. The apparatus of claim 4 wherein the flight tube axis of the time-of-flight mass spectrometer is positioned orthogonally to the drift tube of the ion mobility chamber.

6. The apparatus of claim 1 further comprising adjusting means for offsetting the outer ring electrodes, relative to the inner ring electrodes, a variable distance up to and including a unit inner ring electrode width, thereby creating a nonlinear penetrating electric field between each inner metal ring.

7. The apparatus of claim 1 wherein the outer and inner ring electrodes are resistively coated metal helixes.

8. The apparatus of claim 7 further comprising means of offsetting the outer helix a variable distance up to and including to a unit inner helix thickness, thereby creating a nonlinear penetrating electric field within the gaps of said inner helix.

9. The apparatus of claim 1 wherein the ion source is a high pressure matrix assisted laser desorption ionization source.

10. An apparatus for separating and analyzing ions, comprising:
    an ion source to generate ions;
    an ion mobility chamber positioned to receive the ions from the ion source and capable of producing a periodic focusing electric field wherein the ion mobility chamber comprises:
    a plurality of ring electrodes equally spaced to form a drift tube;
    a plurality of inter-electrode gaps adjacent to the ring electrodes wherein the ratio of the drift tube diameter to the electrode width of any individual ring electrode is less than four; and,
    a resistor chain coupled to the outside of the ion mobility chamber to apply a potential to the ring electrodes;
    an endplate coupled to the ion mobility chamber, the endplate having an ion aperture to expel the ions;
    a plurality of lenses coupled to the ion aperture;
    a plurality of electrostatic steering plates coupled to the lenses; and, a detector coupled to the lenses.

11. The apparatus of claim 10 wherein the detector is a mass spectrometer coupled to the lenses.

12. The apparatus of claim 11 wherein the mass spectrometer is a time-of-flight mass spectrometer.

13. The apparatus of claim 12 wherein the flight tube axis of the time-of-flight mass spectrometer is positioned orthogonally to the drift tube axis of the ion mobility chamber.

14. The apparatus of claim 10 wherein the ring electrodes are resistively coated metal helixes.

15. The apparatus of claim 10 wherein the ion source is a high pressure matrix assisted laser desorption ionization source.

16. A method of separating and analyzing ions in the presence of a gas comprising the steps of:

generating ions from an ion source;

separating ions in terms of their mobility using an ion mobility chamber capable of producing a periodic focusing electric field, wherein the ion mobility chamber comprises a plurality of inner ring electrodes coaxial with a plurality of outer ring electrodes and equally spaced to form an inner drift tube wherein the ratio of the drift tube diameter to the electrode width of any individual inner ring electrode is less than four; and, detecting the ions.

17. The method of claim 16 wherein the step of detecting comprises detecting with a mass spectrometer.

18. The method of claim 16 wherein the step of detecting with a mass spectrometer comprises detecting with a time-of-flight mass spectrometer having a flight tube axis positioned orthogonally to the axis defined by the direction in which the ions are transported.

19. The method of claim 16 wherein the step of transporting comprises:

applying a potential to a plurality of ring electrodes separated by a plurality of inter-electrode gaps wherein said plurality of ring electrodes comprises a single series of coaxial rings.

20. The method of claim 16 wherein the step of transporting comprises:

applying a potential to a plurality of outer ring electrodes and to a plurality of inner ring electrodes.

21. The method of claim 20 further comprising the step of:

offsetting the outer ring electrodes, relative to the inner ring electrodes, a variable distance up to and including a unit inner electrode width whereby a nonlinear penetrating electric field is produced between each inner ring electrode.

22. The method of claim 20 wherein the outer and inner ring electrodes are resistively coated metal helixes and wherein the step of offsetting the outer ring electrodes comprises:

offsetting the outer helix a distance equal to a unit inner helix thickness thereby creating a nonlinear penetrating electric field within the gaps of the inner helix.

23. The method of claim 16 wherein the step of generating ions from an ion source comprises generating ions from a high pressure matrix assisted laser desorption ionization source.

24. A method for transporting ions in the presence of a gas comprising:

transporting ions in a periodic focusing electric field; said field being formed in an ion mobility chamber, said ion mobility chamber comprising a plurality of inner ring electrodes coaxial with a plurality of outer ring electrodes and equally spaced to form an inner drift tube wherein the ratio of the drift tube diameter to the electrode width of any individual inner ring electrode is less than four;

increasing the transmission efficiency of the ions from a high pressure source to high vacuum.

25. The method of claim 24 wherein the step of increasing the transmission efficiency of the ions from a high pressure source to high vacuum comprises:

applying a potential to a plurality of ring electrodes separated by a plurality of inter-electrode gaps wherein said plurality of ring electrodes comprises a single series of coaxial ring electrodes.

26. The method of claim 24 wherein the step of increasing the transmission efficiency of the ions from a high pressure source to high vacuum comprises:

applying a potential to a plurality of outer ring electrodes and to a plurality of inner ring electrodes; and, offsetting the outer metal rings a variable distance up to and including a unit inner ring electrode width, whereby a nonlinear penetrating electric field is produced between each inner ring electrode.

27. The method of claim 24 wherein the step of increasing the transmission efficiency of the ions from a high pressure source to high vacuum comprises:

applying a potential to an outer resistivity coated metal helix and an inner resistivity coated metal helix; and, offsetting the outer helix a variable distance up to and including a unit inner helix thickness, whereby a nonlinear penetrating electric field is produced within the gaps of said inner helixes.

* * * * *

UNITED STATES PATENT AND TRADEMARK OFFICE
CERTIFICATE OF CORRECTION

PATENT NO. : 6,639,213 B2  Page 1 of 1
APPLICATION NO. : 09/798032
DATED : October 28, 2003
INVENTOR(S) : Kent J. Gillig et al.

It is certified that error appears in the above-identified patent and that said Letters Patent is hereby corrected as shown below:

On the Title Page, Item (73) should read
-- Assignee: The Texas A&M University System, College Station, TX (US) --

Signed and Sealed this

Fifteenth Day of July, 2008

JON W. DUDAS
*Director of the United States Patent and Trademark Office*